(12) United States Patent
Udell

(10) Patent No.: US 8,506,995 B2
(45) Date of Patent: *Aug. 13, 2013

(54) COENZYME Q10 FORMULATION AND PROCESS METHODOLOGY FOR SOFT GEL CAPSULES MANUFACTURING

(75) Inventor: Ronald G. Udell, Beverly Hills, CA (US)

(73) Assignee: Soft Gel Technologies, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/780,393

(22) Filed: Jul. 19, 2007

(65) Prior Publication Data

US 2008/0003279 A1    Jan. 3, 2008

Related U.S. Application Data

(60) Continuation of application No. 11/738,216, filed on Apr. 20, 2007, now abandoned, which is a continuation of application No. 11/190,396, filed on Jul. 27, 2005, now Pat. No. 7,220,429, which is a continuation of application No. 10/641,328, filed on Aug. 14, 2003, now Pat. No. 6,955,820, which is a division of application No. 09/536,597, filed on Mar. 28, 2000, now Pat. No. 6,616,942.

(60) Provisional application No. 60/126,656, filed on Mar. 29, 1999.

(51) Int. Cl.
*A61K 9/48* (2006.01)

(52) U.S. Cl.
USPC .......................................... 424/451; 424/452

(58) Field of Classification Search
USPC ......................................................... 424/451
See application file for complete search history.

(56) References Cited

U.S. PATENT DOCUMENTS

| | | | |
|---|---|---|---|
| 4,029,760 A | 6/1977 | De Roeck born Holtzhauer | |
| 4,343,816 A | 8/1982 | Cavazza | |
| 4,559,222 A | 12/1985 | Enscore et al. | |
| 4,565,700 A | 1/1986 | Suzuki | |
| 4,599,232 A | 7/1986 | Bertelli | |
| 4,687,782 A | 8/1987 | Brantman | |
| 4,824,669 A | 4/1989 | Folkers et al. | |
| 4,840,970 A * | 6/1989 | Ohasi et al. | 514/690 |
| 5,030,458 A | 7/1991 | Shug et al. | |
| 5,240,961 A | 8/1993 | Shug | |
| 5,290,605 A | 3/1994 | Shapira | |
| 5,298,246 A | 3/1994 | Yano et al. | |
| 5,310,578 A | 5/1994 | Thurn-Muller et al. | |
| 5,362,753 A | 11/1994 | Blum et al. | |
| 5,378,461 A | 1/1995 | Neigut | |
| 5,391,550 A | 2/1995 | Carniglia et al. | |
| 5,431,916 A | 7/1995 | White | |
| 5,500,416 A | 3/1996 | Miyazawa et al. | |
| 5,504,072 A | 4/1996 | Schmidl et al. | |
| 5,512,691 A | 4/1996 | Barnicki et al. | |
| 5,532,002 A | 7/1996 | Story | |
| 5,552,167 A * | 9/1996 | Taylor et al. | 426/99 |
| 5,560,928 A | 10/1996 | Defelice | |
| 5,591,772 A * | 1/1997 | Lane et al. | 514/458 |
| 5,626,849 A | 5/1997 | Hastings et al. | |
| 5,637,316 A | 6/1997 | Ribier et al. | |
| 5,645,856 A * | 7/1997 | Lacy et al. | 424/455 |
| 5,670,320 A | 9/1997 | Wallace et al. | |
| 5,686,491 A | 11/1997 | Sherwood | |
| 5,716,928 A | 2/1998 | Benet et al. | |
| 5,756,291 A | 5/1998 | Griffin | |
| 5,843,476 A | 12/1998 | Ribier et al. | |
| 5,858,401 A | 1/1999 | Bhalani et al. | |
| 5,889,062 A | 3/1999 | Hoppe et al. | |
| 5,891,469 A | 4/1999 | Amselem | |
| 5,912,272 A | 6/1999 | Hoppe et al. | |
| 5,916,591 A * | 6/1999 | Bierdel-Willkommen et al. | 424/456 |
| 5,948,443 A | 9/1999 | Riley et al. | |
| 5,968,987 A | 10/1999 | Charman et al. | |
| 5,976,568 A | 11/1999 | Riley | |
| 5,977,162 A | 11/1999 | Seidman | |
| 5,980,939 A | 11/1999 | Kim et al. | |
| 5,985,344 A | 11/1999 | Cherukuri et al. | |
| 6,008,192 A | 12/1999 | Al-Razzak et al. | |
| 6,020,383 A | 2/2000 | Stone et al. | |
| 6,033,678 A | 3/2000 | Lorenzen | |
| 6,048,846 A | 4/2000 | Cochran | |

(Continued)

FOREIGN PATENT DOCUMENTS

DE    3512054        10/1986
EP    0882450 A2 *  12/1998

(Continued)

OTHER PUBLICATIONS

R. Chopra et al., "A New Coenzyme Q10 Preparation with Enhanced Bioavailability," FASEB Journal, 11 (3), pp. A586, 1997, Abstract.

M. Weis, et al., "Bioavailability of Four Oral Coenzyme Q10 Formulations in Healthy Volunteers," Molec. Aspects. Med., vol. 15, (Supplement) pp. s273-s280, 1994.

Bhandari, et al., "Preparation, Characterization and Evaluation of Coenzyme Q10 Binary Solid Dispersions for Enhanced Solubility and Dissolution," *Biol Pharm. Bull.*, 2007, vol. 30, No. 6, pp. 1171-1176.

Bliznakov, et al., "Biochemical and Clinical Consequencs of Inhibiting Coenzyme Q10 Biosynthesis by Lipid-Lowering HMG-CoA Reductase Inhibitors (Statins): A Critical Overview," *Advances in Therapy*, Jul./Aug. 1998, vol. 15, No. 4, pp. 218-228.

(Continued)

*Primary Examiner* — Susan Tran
(74) *Attorney, Agent, or Firm* — Dorsey & Whitney LLP

(57) ABSTRACT

A formulation of Coenzyme $Q_{10}$, beta-carotenes, Vitamin E, and medium chain triglycerides in rice bran oil and an optional thickener, such as bee's wax, is provided in a soft gel capsule so that a maximum of the Coenzyme $Q_{10}$ is absorbed by the human body. Generally, about 60 mg of Coenzyme $Q_{10}$ is the normal amount provided daily to a healthy sedentary adult.

1 Claim, No Drawings

(56) References Cited

U.S. PATENT DOCUMENTS

| | | | |
|---|---|---|---|
| 6,048,886 A | 4/2000 | Neigut | |
| 6,054,136 A | 4/2000 | Farah et al. | |
| 6,056,971 A * | 5/2000 | Goldman | 424/439 |
| 6,063,432 A | 5/2000 | Maxwell et al. | |
| 6,069,167 A | 5/2000 | Sokol | |
| 6,080,788 A | 6/2000 | Sole et al. | |
| 6,096,338 A | 8/2000 | Lacy et al. | |
| 6,121,234 A | 9/2000 | Benet et al. | |
| 6,174,547 B1 | 1/2001 | Dong et al. | |
| 6,184,255 B1 * | 2/2001 | Mae et al. | 514/720 |
| 6,197,349 B1 | 3/2001 | Westesen et al. | |
| 6,200,550 B1 | 3/2001 | Masterson et al. | |
| 6,203,818 B1 | 3/2001 | Vester | |
| 6,207,137 B1 | 3/2001 | Shuch et al. | |
| 6,218,436 B1 * | 4/2001 | Howard et al. | 514/725 |
| 6,232,346 B1 | 5/2001 | Sole et al. | |
| 6,261,575 B1 | 7/2001 | Hoppe et al. | |
| 6,267,985 B1 | 7/2001 | Chen et al. | |
| 6,277,431 B1 | 8/2001 | Berry et al. | |
| 6,284,268 B1 | 9/2001 | Mishra et al. | |
| 6,300,377 B1 | 10/2001 | Chopra | |
| 6,335,361 B1 | 1/2002 | Hamilton | |
| 6,342,526 B1 | 1/2002 | Vervuert et al. | |
| 6,365,181 B1 | 4/2002 | Matthews | |
| 6,368,618 B1 | 4/2002 | Jun et al. | |
| 6,426,362 B1 | 7/2002 | Miller et al. | |
| 6,428,779 B1 | 8/2002 | Sauermann et al. | |
| 6,436,431 B1 | 8/2002 | Hoffpauer et al. | |
| 6,441,050 B1 | 8/2002 | Chopra | |
| 6,455,589 B1 | 9/2002 | Ames et al. | |
| 6,469,024 B2 | 10/2002 | Tino et al. | |
| 6,472,378 B2 | 10/2002 | von Borstel | |
| 6,479,069 B1 | 11/2002 | Hamilton | |
| 6,503,483 B2 | 1/2003 | Shuch et al. | |
| 6,503,506 B1 | 1/2003 | Germano | |
| 6,503,523 B2 | 1/2003 | Hoppe et al. | |
| 6,506,915 B1 | 1/2003 | West | |
| 6,528,042 B1 | 3/2003 | Brown et al. | |
| 6,545,184 B1 | 4/2003 | Lipshutz | |
| 6,552,004 B1 | 4/2003 | Elazhary et al. | |
| 6,562,869 B1 | 5/2003 | Hamilton et al. | |
| 6,569,463 B2 | 5/2003 | Patel et al. | |
| 6,579,854 B1 | 6/2003 | Mitchell et al. | |
| 6,616,942 B1 * | 9/2003 | Udel | 424/451 |
| 6,623,734 B2 * | 9/2003 | Udell et al. | 424/94.1 |
| 6,630,170 B2 | 10/2003 | Balkus et al. | |
| 6,664,287 B2 | 12/2003 | Avery et al. | |
| 6,730,319 B2 | 5/2004 | Maeder et al. | |
| 6,740,338 B1 | 5/2004 | Chopra | |
| 6,782,307 B2 | 8/2004 | Wilmott et al. | |
| 6,790,465 B2 | 9/2004 | Weissman | |
| 6,855,733 B2 | 2/2005 | Udell et al. | |
| 6,955,820 B1 | 10/2005 | Udell | |
| 7,015,245 B2 | 3/2006 | Rich et al. | |
| 7,026,361 B2 | 4/2006 | Minemura et al. | |
| 7,060,263 B2 * | 6/2006 | Udell et al. | 424/94.1 |
| 7,169,385 B2 | 1/2007 | Fantuzzi et al. | |
| 7,182,950 B2 | 2/2007 | Garti et al. | |
| 7,220,429 B2 | 5/2007 | Udell | |
| 7,273,606 B2 | 9/2007 | Fantuzzi et al. | |
| 7,273,622 B2 | 9/2007 | Udell et al. | |
| 7,588,786 B2 | 9/2009 | Khan et al. | |
| 7,713,523 B2 | 5/2010 | Fantuzzi et al. | |
| 7,815,943 B2 | 10/2010 | Hennen | |
| 8,097,279 B2 | 1/2012 | Hassan et al. | |
| 8,124,072 B2 | 2/2012 | Fantuzzi | |
| 8,147,826 B2 | 4/2012 | Fantuzzi | |
| 8,343,541 B2 | 1/2013 | Fantuzzi | |
| 2002/0048798 A1 | 4/2002 | Avery et al. | |
| 2002/0098172 A1 | 7/2002 | Udell et al. | |
| 2003/0082168 A1 | 5/2003 | Yegorova | |
| 2003/0108600 A1 | 6/2003 | Okibayashi et al. | |
| 2003/0119781 A1 | 6/2003 | Udell et al. | |
| 2003/0147927 A1 | 8/2003 | Khan et al. | |
| 2003/0176500 A1 | 9/2003 | Molly et al. | |
| 2003/0232076 A1 | 12/2003 | Makino et al. | |
| 2003/0232095 A1 | 12/2003 | Garti et al. | |
| 2004/0001874 A1 | 1/2004 | Davidson et al. | |
| 2004/0047922 A1 | 3/2004 | Elstner | |
| 2004/0106674 A1 | 6/2004 | Rich et al. | |
| 2004/0126432 A1 | 7/2004 | Hennen | |
| 2004/0166157 A1 | 8/2004 | Thombre | |
| 2005/0025756 A1 | 2/2005 | Erwin | |
| 2005/0031681 A1 | 2/2005 | Udell et al. | |
| 2005/0036998 A1 | 2/2005 | Udell | |
| 2005/0037066 A1 | 2/2005 | Udell et al. | |
| 2005/0069582 A1 | 3/2005 | Fantuzzi | |
| 2005/0070611 A1 | 3/2005 | Fantuzzi | |
| 2005/0169983 A1 | 8/2005 | Hassan et al. | |
| 2006/0013888 A1 | 1/2006 | Fantuzzi et al | |
| 2007/0269508 A1 | 11/2007 | Udell | |
| 2008/0020022 A1 | 1/2008 | Udell | |
| 2008/0089877 A1 | 4/2008 | Udell et al. | |
| 2008/0152707 A1 | 6/2008 | Fantuzzi et al. | |
| 2008/0226710 A1 | 9/2008 | Fantuzzi | |
| 2012/0121566 A1 | 5/2012 | Fantuzzi | |
| 2012/0128769 A1 | 5/2012 | Fantuzzi | |
| 2012/0153519 A1 | 6/2012 | Fantuzzi | |

FOREIGN PATENT DOCUMENTS

| | | |
|---|---|---|
| EP | 0 888 774 | 1/1999 |
| EP | 0888774 A2 * | 1/1999 |
| EP | 1 728 506 | 3/2006 |
| JP | 55081813 A | 6/1980 |
| JP | 57042616 | 3/1982 |
| JP | S57042616 | 3/1982 |
| JP | 5770815 | 5/1982 |
| JP | S57142911 | 9/1982 |
| JP | 59172417 A * | 9/1984 |
| WO | WO 88/03015 | 5/1988 |
| WO | WO 98/40086 | 9/1998 |
| WO | WO 98/56368 | 12/1998 |
| WO | WO 00/51574 | 9/2000 |
| WO | WO 02/09685 | 2/2002 |
| WO | WO 03/105607 | 12/2003 |
| WO | WO 2004/066925 | 8/2004 |
| WO | WO 2005/032278 | 4/2005 |
| WO | WO 2005/092123 | 10/2005 |

OTHER PUBLICATIONS

Chopra, et al., "Relative Bioavailability of Coenzyme Q10 Formulations in Human Subjects," *Internat. J. Vit. Nutr. Res.*, 1998, vol. 68, pp. 109-113.

CRC Handbook of Chemistry and Physics, 51st Edition, R.C. Weast (Editor), The Chemical Rubber Co., Cleveland, Ohio, 1970, pp. C-309, 356, 364, 392, 434 and 488.

Dictionary.com accessed on Jan. 17, 2007, "thixotropic" 1 page.

Grant & Hackh's Chemical Dictionary, Definition of Gelatin, Fifth Edition, McGraw-Hill Book Company, 1987, p. 258.

Greenberg, et al., "Co-enzyme Q10: a new drug for cardiovascular disease," *The Journal of Clinical Pharmacology*, 1990, vol. 30, pp. 596-608.

Kommuru, et al., "Self-emulsifying drug delivery systems (SEDDS) of coenzyme Q10: formulation development and bioavailabiilty assessment," *International Journal of Pharmaceutics*, 2001, vol. 212, pp. 233-246.

Merriam-Webster Dictionary OnLine, definition of "elixir," http://www.merriam-webster.com/dictionary/elixir, printed from the Jun. 3, 2009, 2 pages.

RITO Partnership, Rice Bran Oil Info, http://web.archive.org/web/20020809203831/http://www.ricebranoil.info/why/index.html, web page of Aug. 9, 2002, printed from the Internet on Apr. 29, 2009.

Office Action dated May 18, 2001, U.S. Appl. No. 09/536,597, 8 pages.

Amendment dated Oct. 18, 2001, U.S. Appl. No. 09/536,597, 10 pages.

Notice of Non-Compliant Amendment dated Sep. 18, 2002, U.S. Appl. No. 09/536,597, 2 pages.

Response dated Nov. 26, 2002, U.S. Appl. No. 09/536,597, 11 pages.

Notice of Allowance and Fee(s) Due with Interview Summary dated Jun. 17, 2003, U.S. Appl. No. 09/536,597, 11 pages.

Preliminary Amendment dated Aug. 14, 2003, U.S. Appl. No. 10/641,328, 4 pages.
Office Action dated Dec. 3, 2004, U.S. Appl. No. 10/641,328, 7 pages.
Amendment and Response dated Mar. 3, 2005, U.S. Appl. No. 10/641,328, 6 pages.
Terminal Disclaimers (two) dated Apr. 8, 2005, U.S. Appl. No. 10/641,328, 4 pages.
Notice of Allowance and Fee(s) Due dated Apr. 21, 2005, 8 pages.
Preliminary Amendment dated Jul. 27, 2005, U.S. Appl. No. 11/190,396, 6 pages.
Office Action dated Aug. 17, 2006, U.S. Appl. No. 11/190,396, 12 pages.
Amendment and Response dated Nov. 16, 2006, U.S. Appl. No. 11/190,396, 13 pages.
Terminal Disclaimers (four) dated Nov. 16, 2006, U.S. Appl. No. 11/190,396, 8 pages.
Terminal Disclaimers (two) dated Dec. 16, 2006, U.S. Appl. No. 11/190,396, 4 pages.
Notice of Allowance and Fee(s) Due and Interview Summary, dated Jan. 9, 2007, U.S. Appl. No. 11/190,396, 9 pages.
Office Action dated May 1, 2008, U.S. Appl. No. 11/738,216, 9 pages.
Amendment and Response dated Jul. 10, 2008, U.S. Appl. No. 11/738,216, 15 pages.
Terminal Disclaimers (five) dated Jul. 10, 2008, U.S. Appl. No. 11/738,216, 10 pages.
Final Office Action dated Oct. 27, 2008, U.S. Appl. No. 11/738,216, 8 pages.
Notice of Abandonment dated May 11, 2009, U.S. Appl. No. 11/738,216, 3 pages.
Anderson U.S. Appl. No. 60/253,874, David M. Anderson, Applicant, filed Nov. 29, 2000, 21 pages.
Al-Hasso, Shahla, "Coenzyme Q10: A Review," *Hospital Pharmacy*, vol. 36, No. 1, pp. 51-55, 2000 Facts and Comparisons.
Comax Q10 Trademark Registration Abstract and Specimen, Registration No. 1764014, registered Apr. 13, 1993, 26 pages.
Author Unknown, "pformulate: A Soft Gell!!" 2000, pp. 1-6, found at URL: http://www.pformulate.com/pformsoftgel.htm.
Author Unknown, Paul Karrer Biography, Nobel Prizes, Nobel Prize in Chemistry, nobelprize.org, printed on Jan. 5, 2007, 2 pages.
Author Unknown, Oilseeds International Ltd., Rice bran oil—a health benefit, http://www.oilseedssf.com/products/prod.rice.html, 2002, printed on Mar. 6, 2006; 2 pages.
Constantinescu, et al., "A Randomized Study of the Bioavailability of Different Formulations of Coenzyme Q10 (Ubiquinon)," The Journal of Clinical Pharmacology, 2007; 47: 1580-1586.
Density of Cooking Oil, *The Physics Factbook*, edited by Glenn Elert, dated unknown, 3 pages.
Kang et al., "Physicochemical studies of lidocaine-menthol binary systems for enhanced membrane transport," *International Journal of Pharmaceutics*, 206 (2000) 35-42.
Kaplun-Frischoff, et al., "Testosterone Skin Permeation Enhancement by Menthol through Formation of Eutectic with Drug and Interaction with Skin Lipids," Journal of Pharmaceutical Sciences, vol. 86, No. 12, Dec. 1997, pp. 1394-1399.
Kommuru, et al., "A simplified chromatographic method for quantitative determination of coenzyme Q10 in dog plasma," *Journal of Pharmaceutical and Biomedical Analysis*, 16 (1998) 1037-1040.

Kommuru, et al., "Racemate and Enantiomers of Ketoprofen: Phase Diagram, Thermodynamic Studies, Skin Permeability, and Use of Chiral Permeation Enhancers," *Journal of Pharmaceutical Sciences* vol. 87, No. 7, Jul. 1998, pp. 833-840.
Kommuru, et al., "Stability and Bioequivalence Studies of Two Marketed Formulations of Coenzyme Q10 in Beagle Dogs," *Chem. Pharm. Bull.* 47(7) 1024-1028 (1999).
Nazzal et al., "Preparation and in vitro characterization of a eutectic based semisolid self-nanoemulsified drug delivery system (SNEDDS) of ubiquinone: mechanism and progress of emulsion formation," *International Journal of Pharmaceutics* 235 (2002) 247-265.
Nazzal et al., "Response Surface Methodology for the Optimization of Ubiquinone Self-Nonoemulsified Drug Delivery System," *AAPSPharmSciTech 2002*; 3 (1) article 3, pp. 1-9, Published: Feb. 8, 2002, found at URL: http://www.aapspharmscitech.org.
Pouton, Colin W., "Lipid formulations for oral administration of drugs: non-emulsifying, self-emulsifying and 'self-microemulsifying' drug delivery systems," *European Journal of Pharmaceutical Sciences* 11 Suppl. 2 (2000) S93-S98.
Shojaei et al., "Transbuccal permeation of a nucleoside analog, dideoxycytidine: effects of menthol as a permeation enhancer," *International Journal of Pharmaceutics* 192 (1999) 139-146.
Shrestha et al., "Aqueous Phase Behavior of Diglycerol Fatty Acid Esters," *Journal of Dispersion Science and Technology*, 28: pp. 883-891, 2007.
Siekmann et al., "Preparation and Physicochemical Characterization of Aqueous Dispersions of Coenzyme Q10 Nanoparticles," *Pharmaceutical Research*, vol. 12, No. 2, 1995.
Walker, "Mass, Weight, Density or Specific Gravity of Liquids, Specific Gravity of Liquids," 2007, Slmetric.co.uk [http://www.simetric.co.uk/si_liquids.htm], 5 pages.
Weber, et al., "Intestinal Absorption of Coenzyme Q10 Administered in a Meal or as Capsules to Healthy Subject," *Nutrition Research*, vol. 17, No. 6, pp. 941-945, 1997.
Third Party Requestor's Comments under 35 C.F.R. 314(B)(2) and 37 C.F.R. 1.947 in Inter Partes Reexamination of U.S. Patent 8,124,072, Feb. 22, 2013, 74 pages.
Third Party Requestor's Comments under 35 C.F.R. 314(B)(2) and 37 C.F.R. 1.947 in Inter Partes Reexamination of U.S. Patent 8,105,583, Feb. 22, 2013, 52 pages.
Third Party Requestor's Comments under 35 C.F.R. 314(B)(2) and 37 C.F.R. 1.947 in Inter Partes Reexamination of U.S. Patent 8,147,826, Feb. 22, 2013, 33 pages.
Order Construing Claims and Granting Defendants' Motion for Summary Judgment entered Aug. 2, 2012, CV 10-0301 PSG (JCx), *Jarrow Formulas, Inc.* v. *Now Health Group, Inc.*, 28 pages.
Amendment filed Jan. 15, 2008, to Office Action dated Sep. 17, 2007, U.S. Appl. No. 10/293,932, 16 pages.
Amendment filed Mar. 11, 2009, to Office Action dated Sep. 11, 2008, U.S. Appl. No. 10/293,932, 16 pages.
Palamakula, et al., "Preparation and in Vitro Characterization of Self-Nanoemulsified Drug Delivery Systems of Coenzyme Q10 Using Chiral Essential Oil Components," Pharmaceutical Technology, Oct. 2004, pp. 74-88.

* cited by examiner

COENZYME Q10 FORMULATION AND PROCESS METHODOLOGY FOR SOFT GEL CAPSULES MANUFACTURING

CROSS REFERENCE TO RELATED APPLICATIONS

This application claims priority from and is a Continuation of U.S. application Ser. No. 11/738,216, filed Apr. 20, 2007 now abandoned, which is a Continuation of U.S. application Ser. No. 11/190,396, filed Jul. 27, 2005, now U.S. Pat. No. 7,220,429, which is Continuation of U.S. application Ser. No. 10/641,328, filed on Aug. 14, 2003, now U.S. Pat. No. 6,955,820, which is a Divisional of U.S. application Ser. No. 09/536,597, filed Mar. 28, 2000, now U.S. Pat. No. 6,616,942, which claims priority from U.S. Provisional Application Ser. No. 60/126,656, filed Mar. 29, 1999, the contents of which are herein incorporated by reference in their entirety.

BACKGROUND OF THE INVENTION

This invention relates to an improved formulation and process methodology of Coenzyme $Q_{10}$ in producing soft gel capsules of this formulation. Coenzyme $Q_{10}$ ($CoQ_{10}$ or Ubiquinone) is a large molecular weight (863.63 grams) lipid compound that is produced in the liver and perhaps other body organs. The total body content is estimated to be 1.4 to 1.8 grams, depending on the age and the physical fitness of the individual. Although $CoQ_{10}$ is found in the mitochondria and other organelles of every living cell, it appears to be most abundant in tissues with a high number of mitochondria and a high level of metabolic activity. For example, in the metabolically inactive blood there is approximately 4 mg, in the heart, and in the skeletal muscle 1000 mg. The blood acts as a $CoQ_{10}$ reservoir and transport media between endogenous $CoQ_{10}$ synthesis in the liver, exogenous $CoQ_{10}$ absorption from digested food substances in the intestinal tract, and the body cells. Endogenous synthesis appears to be responsible for 56 percent and exogenous sources for 44 percent of the body's $CoQ_{10}$ requirements. These numbers are currently being studied and endogenous $CoQ_{10}$ synthesis may be significantly deficient in the elderly. These deficiencies are not related to the total caloric intake, but rather to the vitamin content of ingested foods. The body requires multiple vitamins for the synthesis of $CoQ_{10}$.

$CoQ_{10}$ requirements of the body are also variable between individuals and are dependent on age, physical activity, and disease. It is estimated that the body $CoQ_{10}$ utilization is between 5 and 9 mg per day. Intercellular $CoQ_{10}$ is required for the synthesis of energy and therefore essential for life. Energy synthesis occurs in the mitochondria, where $CoQ_{10}$ provides an electron for the electron transport chain in the cytochrome system, in which adenosine triphosphate (ATP) is synthesized. As $CoQ_{10}$ gives up an electron for ATP synthesis, it gets oxidized. If $CoQ_{10}$ is used as an antioxidant, it gets oxidized and is no longer available to provide electrons and function in the synthesis of ATP. Under conditions of high metabolic stress, endogenous sources may become inadequate to meet the body's $CoQ_{10}$ requirement for ATP synthesis. Under such conditions, dietary $CoQ_{10}$ supplementation has been shown to be an effective source. An improved soft gel formulation and process of $CoQ_{10}$ soft gel capsule manufacturing has uses to treat heart failure, chronic fatigue and patients with psoriasis and planter warts. In all cases, it has been found that the improved soft gel formulation at ingestion rates of 30-100 mg/day of $CoQ_{10}$ have been proven to be superior to commercially available 60 mg dry powder capsules, and existing 100 mg/day $CoQ_{10}$ soft gel formulations.

An appropriate $CoQ_{10}$ dosage for a normal individual compared to the dosage necessary for a diseased individual has been difficult to ascertain. Recommended doses of 10 to 30 mg/day were found to be ineffective for patients with significant $CoQ_{10}$ deficiencies. In the past 15 years, it has become generally accepted that poor intestinal absorption of certain $CoQ_{10}$ formulations limits their effective use. For this reason, 50 and 150 mg $CoQ_{10}$ containing tablets or capsules are commercially available to the consumer, at a considerably higher cost.

Folkers et al (U.S. Pat. No. 4,824,669) addresses a soft gel capsule with $CoQ_{10}$ and at least one vegetable oil. This formulation was determined to increase blood $CoQ_{10}$ levels to 2.5 µg/ml compared to 1.6 µg/ml for an equivalent 100 mg dose of dry powder $CoQ_{10}$. Many different $CoQ_{10}$ formulations have appeared which are claimed to increase intestinal absorption. However, intestinal absorption data, collected under near basal conditions, which compare $CoQ_{10}$ alone in oil with dry powder $CoQ_{10}$, are conclusive that oil is a better delivery agent.

SUMMARY OF THE INVENTION

The present invention comprises a stable and nontoxic soft gel Coenzyme $Q_{10}$ formulation and process methodology of Coenzyme $Q_{10}$ for maximum Coenzyme $Q_{10}$ levels in the human body for a given input. A preferred soft gel formulation includes Coenzyme $Q_{10}$ (hereinafter $CoQ_{10}$), Vitamin E, beta-carotene, bee's wax, medium chain triglycerides available as MCT Myglyol S12, and rice bran oil formulated to maximize the body's absorption by maintaining the $CoQ_{10}$ in what may be a supersaturated solution in easily absorbed materials, that can provide healthful effects, as opposed to just fillers. It is important as much of the supplied $CoQ_{10}$ be absorbed, rather than just taking megadoses at frequent intervals as the wholesale cost of $CoQ_{10}$ dry powder in quantity is as much as $2000 per kg. Not only is a relatively large percentage of the $CoQ_{10}$ absorbed, but the volume of the soft gel capsule is minimized, making it easier to swallow and requiring smaller shipping and storage space. Recent studies indicate the preferred soft gel $CoQ_{10}$ formulation should be administered twice a day in dosages of about 30 mg $CoQ_{10}$ in 220 mg capsules, as that amount of $CoQ_{10}$ is about the maximum the body of a healthy sedentary adult can use for maintenance of a preferred blood level. For those who have deficiencies of $CoQ_{10}$, studies have shown that twice a day administration of about 60 mg $CoQ_{10}$ in 435 mg capsules is advantageous. In special instances of $CoQ_{10}$ deficiency, twice a day ingestion of 100 mg $CoQ_{10}$ containing soft gel capsules can be tolerated.

It is therefore an object of the present invention to provide a soft gel formulation of $CoQ_{10}$ and a methodology of formulation processing that produce a significantly greater bioavailability percentage of ingested $CoQ_{10}$ than existing soft or dry formulations.

Another object of the present invention is to provide a soft gel formulation of $CoQ_{10}$ and methodology of administration that produces greater absorption of $CoQ_{10}$ into the intestine.

Another object is to minimize the ingested volume required to maintain a given $CoQ_{10}$ blood content.

Another object is to provide a process that keeps $CoQ_{10}$ in solution in readily absorbed materials, that themselves have beneficial effects.

These and other objects and advantages of the present invention will become apparent to those skilled in the art after considering the following detailed description of the invention.

DETAILED DESCRIPTION OF THE PREFERRED EMBODIMENTS

The unique formulation of the present invention of a stable and non-toxic soft gel Coenzyme $Q_{10}$ where the amount of Coenzyme $Q_{10}$ is balanced with antioxidants and absorption agents to maximize the percentage of Coenzyme $Q_{10}$ in a capsule of a given size, that is delivered to the blood stream from the intestines. The formulation includes: Coenzyme $Q_{10}$, Vitamin E, beta-carotene, bee's wax, medium chain triglycerides (MCT) such as MCT Myglyol S12, and rice bran oil. The preferred soft gel Coenzyme $Q_{10}$ formulation of the present invention is prepared in accordance with the following sequence of ingredients and process.

Rice bran oil, a carrier suspension agent for soft gel formulation useful for absorption of lipophilic ingredients such as Coenzyme $Q_{10}$, is heated to 50 to 60° C. Bee's wax is then added. 50° C. is above the melting point of bee's wax and the wax and oil is mixed until a uniform mixture is formed. Bee's wax thickens the rice bran oil and acts as a suspension agent for subsequent ingredients. Without bee's wax, the other ingredients, which are to suspended inside a transparent gel capsule, might separate or congregate under the effect of gravity, and appear faulty or spoiled to the consumer.

Subsequently, the mixture is cooled to 35 to 45° C. Coenzyme $Q_{10}$, beta-carotenes including alpha and beta carotenes, cryptoxanthin, lutein and zeaxanthin (available commercially as Betatene, available from Cognis Nutrition), Vitamin E, and medium chain triglycerides (MCT) are then simultaneously added to the oil-wax mixture under a vacuum (to eliminate oxidation) and mixed together for one to two hours. beta-carotenes improves the solubility and adds antioxidant value. Vitamin E is an antioxidant preservative that prevents peroxidation of the final product, adds antioxidant value, and is fat soluble. Although Vitamin E is available commercially in 30 IU, 100 IU, 200 IU, 400 IU, and 1000 IU concentrations, for the present invention concentrations from 350 IU to 400 IU are usable, with 372 IU being the preferred concentration, which results in a concentration from 30 to 100 IU in the soft gel capsule. Medium chain triglycerides are fatty acids that improve the lipid environment and enhance absorbability like the rice bran oil. The bee's wax primarily increases viscosity to keep insoluble components from settling to one side of the soft gel capsule, but it also improves solubility. For instances where viscosity (and in turn gel capsule cosmetics) is not a concern, it can be eliminated.

The resultant mixture is cooled to 25 to 30° C. A nitrogen gas blanket is introduced to shield the mixture for oxygen and the pressure is returned to atmospheric. The mixture is then encapsulated in a soft gel capsule.

Formula 1

| Ingredient | Amount Range | % in formula |
| --- | --- | --- |
| 1. Vitamin E 372 IU | 0.161 g-2.50 g | 37%-51% |
| 2. Beta Carotene (20% from *D. salina*) | 0.00525 g-0.118 g | 1.2%-2.5% |
| 3. MCT Myglyol 812 | 0.5 g-1.0 g | 12%-21% |
| 4. Rice Bran Oil | 0.193 g-.50 g | 10%-44% |
| 5. Yellow Bee's Wax | 0.015 g-.2 g | 1%-4% |
| 6. $CoQ_{10}$ | 0.5-2.0 g | 10%-15% |

Formula 2

| Ingredient | Amount Range | % in formula |
| --- | --- | --- |
| 1. Vitamin E 372 IU | 0.161 g-2.50 g | 38.5%-53% |
| 2. Beta Carotene (20% from *D. salina*) | 0.00525 g-0.118 g | 1.25%-2.6% |
| 3. MCT Myglyol 812 | 0.5 g-1.0 g | 12%-22% |
| 4. Rice Bran Oil | 0.193 g-.50 g | 10%-46% |
| 5. $CoQ_{10}$ | 0.5-1.0 g | 11%-16% |

The bioavailability or intestinal absorption of $CoQ_{10}$ has been a major controversy in the international $CoQ_{10}$ research community. Previous data indicate that only 1 to 3 percent of dry powder $CoQ_{10}$ formulations are absorbed through the lacteals in the intestines and appear in the blood over a twelve hour interval. In general, blood levels of 1.2 to 1.6 µg/ml have been reported, when taking 30 to 60 mg/day dry powder $CoQ_{10}$ formulation for 30 days. It has been reported that when a dry powder $CoQ_{10}$ formulation is taken with a fat, such as peanut butter, steady-state blood levels of 2.0 to 2.8 µg/ml are measurable.

Multiple clinical trials were conducted in the United States and Europe using the Folkers (U.S. Pat. No. 4,824,669) soft gel. With a dosage of 100 mg/day, multiple investigators have reported group mean blood levels of 2.3 to 3.5 µg/ml depending on the laboratory conducting the measurement.

As observed in recent trials, the bioavailability results found for the present soft gel indicate it provides approximately 50 percent, and with two 30 mg $CoQ_{10}$ containing capsules, 100 percent, of the daily $CoQ_{10}$ requirements of a normal sedentary individual. It would take at least three of the dry powder 30 mg $CoQ_{10}$ capsules to produce the same effects as one soft gel, and six to produce the same effect as two 30 mg $CoQ_{10}$ containing soft gel capsules of the present invention. Regardless of the absorption mechanism, the significantly higher basal blood $CoQ_{10}$ levels (167%) and the 273% greater absorption rate were found in previous studies to establish that the present soft gel formulation is indeed a superior product to dry $CoQ_{10}$ formulations. This may be particularly true for those individuals whose daily $CoQ_{10}$ requirement is elevated due to high physical activity, an increased use of $CoQ_{10}$ as an antioxidant, and disease associated with known $CoQ_{10}$ deficiencies.

Cellular $CoQ_{10}$ content is a function of the number and quality of the cellular mitochondria. For example, the failing heart muscle has 2.2 µg $CoQ_{10}$ per mg of tissue and a blood $CoQ_{10}$ deficiency of 0.3-0.5 µg/ml. The normal hearts conditioned heart has 6.3 µg/gm per mg of tissue, and a low basal blood level of 0.5-0.6 µg/ml. These results indicate that supplemental $CoQ_{10}$ enters the cell. This observation has also been reported for skeletal muscles of trained and non-trained athletes.

The subjective and objective responses to supplemental $CoQ_{10}$ in the normal individual appear more rapidly compared to that of the physically unfit or the diseased individual with a $CoQ_{10}$ deficiency. The most probable reason for this observation is that the metabolic machinery (mitochondria) is viable in the non-diseased normal volunteer, whereas the mitochondria are atrophied in the cells of deconditioned and/or diseased individuals. Therefore, it takes time in the diseased individual to build up the mitochondria to a more normal activity level and to normalize their distribution in the organ system involved.

In summary, studies have statistically proven that the present soft gel $CoQ_{10}$ formulation used at 60 mg $CoQ_{10}$/day is superior to dry powder $CoQ_{10}$ formulations, and prior art soft gel formulations.

Thus, there has been shown novel formulations, which fulfill all of the objects and advantages sought therefor. Many changes, alterations, modifications and other uses and applications of the subject invention will become apparent to those skilled in the art after considering the specification. All such changes, alterations and modifications which do not depart from the spirit and scope of the invention are deemed to be covered by the invention which is limited only by the claims that follow.

What is claimed is:

1. A soft gelatin capsule encapsulating a non-powdered composition comprising:
   coenzyme Q10;
   0.193 g-0.50 g of rice bran oil;
   0.161 g-2.50 g of vitamin E;
   0.00525 g-0.118 g of β-carotenes; and
   0.015 g-0.2 g of beeswax.

* * * * *